US010626082B2

(12) United States Patent
Brazdil et al.

(10) Patent No.: US 10,626,082 B2
(45) Date of Patent: Apr. 21, 2020

(54) AMMOXIDATION CATALYST WITH SELECTIVE CO-PRODUCT HCN PRODUCTION

(71) Applicants: James F. Brazdil, Glen Ellyn, IL (US); Mark A. Toft, Somonauk, IL (US); Michael J Seely, Plainfield, IL (US); Charles J Besecker, Batavia, IL (US); Sean S.-Y. Lin, Naperville, IL (US)

(72) Inventors: James F. Brazdil, Glen Ellyn, IL (US); Mark A. Toft, Somonauk, IL (US); Michael J Seely, Plainfield, IL (US); Charles J Besecker, Batavia, IL (US); Sean S.-Y. Lin, Naperville, IL (US)

(73) Assignee: INEOS EUROPE AG, Rolle (CH)

( * ) Notice: Subject to any disclaimer, the term of this patent is extended or adjusted under 35 U.S.C. 154(b) by 252 days.

(21) Appl. No.: 15/290,024

(22) Filed: Oct. 11, 2016

(65) Prior Publication Data

US 2018/0099925 A1    Apr. 12, 2018

(51) Int. Cl.
| | |
|---|---|
| *C07C 253/26* | (2006.01) |
| *C07C 255/00* | (2006.01) |
| *B01J 37/03* | (2006.01) |
| *C07C 205/00* | (2006.01) |
| *B01J 23/00* | (2006.01) |
| *C07C 253/18* | (2006.01) |
| *B01J 23/887* | (2006.01) |
| *B01J 37/04* | (2006.01) |
| *B01J 37/08* | (2006.01) |

(52) U.S. Cl.
CPC ........... *C07C 253/26* (2013.01); *B01J 23/002* (2013.01); *B01J 23/8876* (2013.01); *B01J 23/8878* (2013.01); *B01J 37/031* (2013.01); *B01J 37/035* (2013.01); *B01J 37/04* (2013.01); *B01J 37/08* (2013.01); *C07C 205/00* (2013.01); *C07C 253/18* (2013.01); *C07C 255/00* (2013.01); *B01J 2523/00* (2013.01); *Y02P 20/52* (2015.11)

(58) Field of Classification Search
CPC .............................. C07C 253/26; B01J 23/002
See application file for complete search history.

(56) References Cited

U.S. PATENT DOCUMENTS

| | | | |
|---|---|---|---|
| 4,192,776 A | 3/1980 | Grasselli et al. | |
| 5,658,842 A | 8/1997 | Midorikawa et al. | |
| 5,663,113 A | 9/1997 | Midorikawa et al. | |
| 5,834,394 A | 11/1998 | Chen et al. | |
| 5,840,648 A | 11/1998 | Suresh et al. | |
| 7,473,666 B2 | 1/2009 | Yanagi et al. | |
| 7,576,232 B2 | 8/2009 | Seely et al. | |
| 8,153,546 B2 | 4/2012 | Brazdil et al. | |
| 8,258,073 B2 | 9/2012 | Besecker et al. | |
| 8,350,075 B2 | 1/2013 | Brazdil et al. | |
| 8,420,566 B2 | 4/2013 | Brazdil et al. | |
| 8,455,388 B2 | 6/2013 | Brazdil et al. | |
| 8,546,634 B2 | 10/2013 | Midorikawa et al. | |
| 8,835,666 B2 | 9/2014 | Brazdil et al. | |
| 9,211,527 B1 | 12/2015 | Brazdil et al. | |
| 9,295,977 B2 | 3/2016 | Brazdil et al. | |
| 9,358,528 B2 | 6/2016 | Brazdil et al. | |
| 9,433,929 B2 | 9/2016 | Brazdil et al. | |
| 9,550,729 B2 | 1/2017 | Brazdil et al. | |
| 2002/0103077 A1 | 8/2002 | Kimura et al. | |
| 2002/0198398 A1 | 12/2002 | Paparizos et al. | |
| 2004/0110978 A1 | 6/2004 | Paparizos et al. | |
| 2007/0260085 A1 | 11/2007 | Seely et al. | |
| 2011/0233460 A1 | 9/2011 | Brazdil et al. | |
| 2011/0237821 A1 | 9/2011 | Brazdil et al. | |
| 2013/0072710 A1 | 3/2013 | Brazdil et al. | |
| 2014/0171303 A1 | 6/2014 | Yoshida et al. | |
| 2015/0343427 A1 | 12/2015 | Brazdil et al. | |
| 2016/0175817 A1 | 6/2016 | Brazdil et al. | |

FOREIGN PATENT DOCUMENTS

| | | | |
|---|---|---|---|
| CN | 1810364 | 8/2006 | |
| CN | 103418400 | 12/2013 | |
| EP | 0484792 | 5/1992 | |
| EP | 0713724 | 5/1999 | |
| EP | 1223163 | 7/2002 | |
| EP | 2075064 | 10/2007 | |
| JP | 07303836 | 11/1995 | |
| JP | 2006055732 A | * 3/2006 | .............. B01J 23/88 |
| JP | 2009220052 | 10/2009 | |
| JP | 2010131576 | 6/2010 | |
| WO | 2004050238 | 6/2004 | |
| WO | 2004050240 | 6/2004 | |

OTHER PUBLICATIONS

International Searching Authority, International Search Report and Written Opinion in PCT/US2017/053384; dated Dec. 18, 2017, 13 pages.

* cited by examiner

*Primary Examiner* — Joseph R Kosack
(74) *Attorney, Agent, or Firm* — David P. Yusko

(57) ABSTRACT

A catalytic composition and process useful for the conversion of an olefin selected from the group consisting of propylene, isobutylene or mixtures thereof, to acrylonitrile, methacrylonitrile, hydrogen cyanide and acetonitrile and mixtures thereof, wherein the catalyst exhibiting increased selectivity to hydrogen cyanide compared to prior art catalysts.

23 Claims, No Drawings

AMMOXIDATION CATALYST WITH SELECTIVE CO-PRODUCT HCN PRODUCTION

BACKGROUND OF THE INVENTION

Field of the Invention

The present invention relates to an improved catalyst for use in the ammoxidation of an unsaturated hydrocarbon to the corresponding unsaturated nitrile which unexpectedly provides increased yields of the hydrogen cyanide (HCN) coproduct without a significant decrease in the yield of the unsaturated nitrile. In particular, the present invention is directed to an improved catalytic composition for the ammoxidation of propylene and/or isobutylene to acrylonitrile and/or methacrylonitrile, respectively, as well as hydrogen cyanide (HCN) and acetonitrile coproducts, said catalyst exhibiting increased selectivity to hydrogen cyanide compared to prior art catalysts, wherein said catalyst comprises a complex of metal oxides comprising bismuth, molybdenum, iron, cerium, and other promoter elements, and wherein said catalyst is characterized by the ratio of iron to bismuth and cerium, contained in the catalyst.

Description of the Prior Art

Catalysts containing oxides of iron, bismuth and molybdenum, promoted with suitable elements, have long been used for the conversion of propylene and/or isobutylene at elevated temperatures in the presence of ammonia and oxygen (usually in the form of air) to manufacture acrylonitrile and/or methacrylonitrile. In particular, Great Britain Patent 1436475; U.S. Pat. Nos. 4,766,232; 4,377,534; 4,040,978; 4,168,246; 5,223,469 and 4,863,891 are each directed to bismuth-molybdenum-iron catalysts which may be promoted with the Group II elements to produce acrylonitrile. In addition, U.S. Pat. Nos. 5,093,299, 5,212,137, 5,658,842, 5,834,394, and CN103418400 are directed to bismuth-molybdenum promoted catalysts exhibiting high yields to acrylonitrile.

In part, the instant invention relates to a bismuth-molybdenum-iron catalysts promoted with cerium which contain higher quantities of a cerium-bismuth-molybdenum phase with a scheelite crystal structure than earlier generations of compositionally similar catalysts. Such catalysts are taught in U.S. Pat. Nos. 8,153,546; 8,258,073; 8,350,075; 8,420,566; 8,455,388; 9,211, 572; 9,358,528 and U.S. Pub. No. 2016/0175817.

In part, the instant invention relates to promoted bismuth-molybdenum-iron ammoxidation catalysts providing enhanced hydrogen cyanide production. U.S. Pat. No. 5,840,648 teaches a promoted bismuth-molybdenum-iron ammoxidation catalysts incorporating calcium which provided increased hydrogen cyanide production without a significant decrease in acrylonitrile production. U.S. Pat. No. 7,576,232 teaches the addition of various molybdate compounds to ammoxidation catalysts in order to modify catalyst performance to increase the yield of hydrogen cyanide and to inhibit molybdenum loss from such ammoxidation catalysts.

SUMMARY OF THE INVENTION

The present invention is directed to an improved process and catalyst for the ammoxidation of propylene to acrylonitrile, hydrogen cyanide and acetonitrile. The process and catalyst are characterized by a greater overall conversion of the propylene to hydrogen cyanide and a greater overall conversion of the propylene to acrylonitrile, hydrogen cyanide and acetonitrile than previously achieved with in other processes and catalysts. Historically, catalysts which provided an increase in hydrogen cyanide yield did so with a corresponding decrease in the yield of acrylonitrile. The catalysts of the instant invention do not conform to this historical trend. The process and catalyst of the instant invention provide increased hydrogen cyanide production without a significant decrease in the acrylonitrile production and provide an overall increase in the production of acrylonitrile, hydrogen cyanide and acetonitrile.

In one embodiment, the invention is directed to a catalytic composition comprising a complex of metal oxides wherein the relative ratios of the listed elements in said catalyst are represented by the following formula:

$$Mo_mBi_aFe_bA_cD_dE_eF_fG_gCe_hCr_nQ_qO_x$$

wherein A is at least one element selected from the group consisting of lithium, sodium, potassium, rubidium and cesium;

D is at least one element selected from the group consisting of nickel, cobalt, manganese, zinc, magnesium, calcium, strontium, cadmium and barium;

E is at least one element selected from the group consisting of tungsten, boron, aluminum, gallium, indium, phosphorus, arsenic, antimony, vanadium and tellurium;

F is at least one element selected from the group consisting of lanthanum, europium, gadolinium, terbium, dysprosium, holmium, erbium, thulium, ytterbium, lutetium, scandium, yttrium, titanium, zirconium, hafnium, niobium, tantalum, aluminum, gallium, indium, thallium, silicon, lead and germanium;

G is at least one element selected from the group consisting of silver, gold, ruthenium, rhodium, palladium, osmium, iridium, platinum and mercury;

Q is at least one of samarium, praseodymium and neodymium and a, b, c, d, e, f, g, h, n, m and x are, respectively, the atomic ratios of bismuth (Bi), iron (Fe), A, D, E, F, G, cerium (Ce), chromium (Cr), molybdenum (Mo) and oxygen (O), relative to "m" atoms of molybdenum (Mo), wherein a is 0.05 to 7,
b is 0.1 to 7,
c is 0 to 5,
d is 0.1 to 12,
e is 0 to 5,
f is 0 to 5,
g is 0 to 0.2,
h is 0.01 to 5,
m is 10-15,
n is 0 to 5,
q is 0 to 2.476, and
x is the number of oxygen atoms required to satisfy the valence requirements of the other component elements present; and wherein $0.4 < b/(a+h)$ and $0.3 \leq (a+h)/d$.

In other embodiments of the above composition, independently $0.3 \leq (a+h)/d \leq 1$, $0.8 \leq h/b \leq 5$, $0.5 \leq a/h < 1.5$, $0.45 \leq (a+h)/d \leq 1$, $0 \leq q/(a+h+q) < 0.16$, and/or $0 \leq m-(3a+2b+c+2d+3h+3n)/2 \leq 1.0$.

The invention also relates to a propylene ammoxidation catalyst formulation capable of providing a variable and reversible range of yield of useful nitriles products including acrylonitrile and HCN. This variation in yield can be effected during operation of the catalyst by the appropriate addition of specific catalyst additives. Specifically, the yield of hydrogen cyanide is increased relative to the amount of acrylonitrile and methacrylonitrile produced in the process by the addition to the catalyst of at least one molybdate compound represented by the formula:

$$A_2Mo_zO_{4+3(z-1)}$$

wherein A is Rb, Li, Na, K, Cs, or a mixture thereof, and z is from 1 to about 8.

The alkali molybdate may be employed with or without a support.

Further, where a molybdate has been added to the catalyst for the purpose of increasing the hydrogen cyanide production this trend is reversible by the addition of a molybdenum oxide compound selected from the group consisting of $MoO_3$, ammonium molybdate, ammonium heptamolybdate, ammonium dimolybdate and mixtures thereof to the catalyst and alkali molybdate mixture catalyzing the ammoxidation process. Thus the addition of a molybdenum oxide to the catalyst and alkali molybdate mixture increases the yield of acrylonitrile and methacrylonitrile relative to the amount of hydrogen cyanide produced in the process (i.e. the amount of acrylonitrile and methacrylonitrile and hydrogen cyanide produced will approach or be restored to their pre-molybdate addition levels).

DETAILED DESCRIPTION OF THE INVENTION

The present invention is directed to an improved mixed metal oxide catalyst and process for the ammoxidation of propylene and/or isobutylene. In particular, the present invention is directed to an improved catalytic composition for the ammoxidation of propylene and/or isobutylene to acrylonitrile and/or methacrylonitrile, respectively, as well as hydrogen cyanide (HCN) and acetonitrile coproducts, said catalyst exhibiting increased selectivity to hydrogen cyanide compared to prior art catalysts, wherein said catalyst comprises a complex of metal oxides comprising bismuth, molybdenum, iron, cerium, and other promoter elements, and wherein said catalyst is characterized by the ratio of iron to bismuth and cerium, contained in the catalyst. As used herein, "catalytic composition" and "catalyst" are synonymous and used interchangeably.

The Catalyst:

In part, the present invention is directed to a multi-component mixed metal oxide ammoxidation catalytic composition comprising a complex of catalytic oxides wherein the elements and the relative ratios of the elements in said catalytic composition are represented by the following formula:

$$Mo_mBi_aFe_bA_cD_dE_eF_fG_gCe_hCr_nQ_qO_x$$

wherein A is at least one element selected from the group consisting of lithium, sodium, potassium, rubidium and cesium;

D is at least one element selected from the group consisting of nickel, cobalt, manganese, zinc, magnesium, calcium, strontium, cadmium and barium;

E is at least one element selected from the group consisting of tungsten, boron, aluminum, gallium, indium, phosphorus, arsenic, antimony, vanadium and tellurium;

F is at least one element selected from the group consisting of lanthanum, europium, gadolinium, terbium, dysprosium, holmium, erbium, thulium, ytterbium, lutetium, scandium, yttrium, titanium, zirconium, hafnium, niobium, tantalum, aluminum, gallium, indium, thallium, silicon, lead and germanium;

G is at least one element selected from the group consisting of silver, gold, ruthenium, rhodium, palladium, osmium, iridium, platinum and mercury;

Q is at least one of samarium, praseodymium and neodymium and a, b, c, d, e, f, g, h, n, m and x are, respectively, the atomic ratios of bismuth (Bi), iron (Fe), A, D, E, F, G, cerium (Ce), chromium (Cr), molybdenum (Mo) and oxygen (O), relative to "m" atoms of molybdenum (Mo), wherein a is 0.05 to 7,
b is 0.1 to 7,
c is 0 to 5,
d is 0.1 to 12,
e is 0 to 5,
f is 0 to 5,
g is 0 to 0.2,
h is 0.01 to 5,
m is 10-15,
n is 0 to 5,
q is 0 to 2.476, and
x is the number of oxygen atoms required to satisfy the valence requirements of the other component elements present; and wherein $0.4 < b/(a+h)$ and $0.3 \leq (a+h)/d$.

In one embodiment, A is at least one element selected from the group consisting of lithium, sodium, potassium, rubidium and cesium. In one embodiment, the catalytic composition is free of potassium.

In one embodiment, D is at least one element selected from the group consisting of nickel, cobalt and magnesium. In one embodiment, D is nickel.

In one embodiment the catalyst contains no tellurium, antimony or selenium. In another embodiment, the components or elements designated by "E" in the above formula may also include tellurium and/or antimony. In another embodiment, the components or elements designated by "E" in the above formula are at least one element selected from the group consisting of chromium, aluminum, gallium, indium, arsenic, antimony and tellurium. In another embodiment, "e" is zero (i.e. the above described composition contains no components or elements designated by "E" in the above formula). In one embodiment, h is from 0.01 to 5. In one embodiment, "F" may additionally include lead (Pb). In another embodiment, "F" does not include lead (Pb). In one embodiment, "m" is 12.

In part, the catalytic composition may be characterized by the relationship of b/(a+h), where "b" is the relative amount of iron in the catalyst, "a" is the relative amount of bismuth in the catalyst, and "h" is the relative amount of cerium. In one embodiment, $0.4 < b/(a+h)$. In another independent embodiment, $0.45 \leq b/(a+h)$.

In part, the catalytic composition may be characterized by the relationship of (a+h)/d, where "a" is the relative amount of bismuth in the catalyst, "h" is the relative amount of cerium in the catalyst and "d" is the relative amounts of nickel, cobalt, manganese, zinc, magnesium, calcium, strontium, cadmium and barium in the catalyst. These relative amounts are the elements subscript in the catalyst formula, or in the case of "d" the sum of the subscripts from the catalyst formula for any nickel, cobalt, manganese, zinc, magnesium, calcium, strontium, cadmium and barium present in the catalyst. In one embodiment, $0.3 \leq (a+h)/d$. In another independent embodiment, $0.15 \leq (a+h)/d$. Other independent embodiments are (each line below being an embodiment):

$0.15 \leq (a+h)/d \leq 1$, $0.3 \leq (a+h)/d \leq 1$, $0.3 \leq (a+h)/d \leq 0.8$, $0.3 \leq (a+h)/d \leq 0.6$, $0.3 \leq (a+h)/d \leq 0.4$, $(a+h)/d \leq 1$, $(a+h)/d \leq 0.8$, $(a+h)/d \leq 0.6$, $(a+h)/d \leq 0.5$, and $(a+h)/d \leq 0.4$.

The catalytic composition may also be characterized by the relationship of "m minus $[(3a+2b+c+2d+3h+3n)/2]$" where "m" is the relative amount of molybdenum in the catalyst, "a" is the relative amount of bismuth in the catalyst, "b" is the relative amount of iron in the catalyst, "c" is the relative amount of "A" elements (i.e. lithium, sodium, potassium, rubidium and cesium) in the catalyst, "d" is the relative amounts of "D" elements (i.e. nickel, cobalt, manganese, zinc, magnesium, calcium, strontium, cadmium and barium) in the catalyst "h" is the relative amount of cerium in the catalyst and "n" is the relative amounts of chromium in the catalyst. These relative amounts are the elements subscript in the catalyst formula, or in the case of "a" the sum of sum of the subscripts from the catalyst formula for any lithium, sodium, potassium, rubidium and cesium present in the catalyst and in the case of "d" the sum of the subscripts from the catalyst formula for any nickel, cobalt, manganese, zinc, magnesium, calcium, strontium, cadmium and barium present in the catalyst. In one embodiment, $0 \leq [m$ minus $[(3a+2b+c+2d+3h+3n)/2]] \leq 1.0$.

In one embodiment, the "Q" is samarium. In other embodiment, the catalyst contains no "Q" element (i.e. "q" is zero). In other embodiments, "q" is greater than zero. In other embodiments, "q" is 0 to 2.476.

The catalytic composition may be characterized by the relationship of $q/(a+h+q)$, where "q" is the relative amount of samarium, praseodymium and neodymium in the catalyst, where "a" is the relative amount of bismuth in the catalyst, and "h" is the relative amount of cerium in the catalyst. These relative amounts are the elements subscript in the catalyst formula, or in the case of "q" the sum of the subscripts from the catalyst formula for any samarium, praseodymium and neodymium present in the catalyst. In one embodiment, $0 \leq q/(a+h+q)$ and $q/(a+h+q) < 0.16$. In another embodiment, $0 \leq q/(a+h+q)$ and $q/(a+h+q) < 0.05$. In another embodiment, $0.01 < q/(a+h+q)$ and $q/(a+h+q) < 0.12$. Other independent embodiments are (each line below being an embodiment):

$0 \leq q/(a+h+q)$, $0.01 < q/(a+h+q)$, $0.02 < q/(a+h+q)$, $0.03 < q/(a+h+q)$, $0.04 < q/(a+h+q)$, $q/(a+h+q) < 0.16$, $q/(a+h+q) < 0.14$, $q/(a+h+q) < 0.12$, $q/(a+h+q) < 0.10$, $q/(a+h+q) < 0.08$, $q/(a+h+q) < 0.06$, and $q/(a+h+q) < 0.05$.

The catalytic composition may also be characterized by the relationship of $h/b$, where "h" is the relative amount of cerium in the catalyst, and "b" is the relative amount of iron in the catalyst. These relative amounts are the elements subscript in the catalyst formula. In one embodiment, $0.8 \leq h/b \leq 5$. Other independent embodiments are (each line below being an embodiment):

$1.2 \leq h/b \leq 5$, $1.5 \leq h/b \leq 5$, $1.2 \leq h/b$, $1.5 \leq h/b$, $0.8 \leq h/b$, and $h/b \leq 5$ It has been discovered that catalysts described within the range described by $0.8 \leq h/b \leq 5$ tend to be stronger in that they have a lower attrition loss as determined by a submerged jet attrition test.

The catalytic composition may also be characterized by the relationship of $(a/h)$, where "a" is the relative amount of bismuth in the catalyst, "h" is the relative amount of cerium in the catalyst. These relative amounts are the elements subscript in the catalyst formula. In one embodiment, $0 < a/h \leq 1.5$. Other independent embodiments are (each line below being an embodiment):

$0.2 \leq a/h \leq 1.5$, $0.3 \leq a/h \leq 1.5$, $0.4 \leq a/h \leq 1.5$, $0.45 \leq a/h \leq 1.5$, $0.5 \leq a/h \leq 1.5$, $0.2 \leq a/h$, $0.3 \leq a/h$, $0.4 \leq a/h$, $0.45 \leq a/h$, $0.65 \leq a/h$, $0.5 \leq a/h$, $0.7 \leq a/h$, $0.8 \leq a/h$, $0.90 \leq a/h$, $a/h \leq 1.2$, and $a/h \leq 1.5$ In an alternative embodiment of the catalyst of the instant invention, the invention is a catalytic composition comprising a complex of metal oxides wherein the relative ratios of the listed elements in said catalyst are represented by the following formula:

$Mo_m Bi_a Fe_b A_c D_d E_e F_f G_g Ce_h Ni_i Co_j Mn_k Mg_l Q_q O_x$ wherein A is at least one element selected from the group consisting of sodium, potassium, rubidium and cesium; and D is at least one element selected from the group consisting of zinc, calcium, strontium, cadmium and barium;

E is at least one element selected from the group consisting of chromium, tungsten, boron, aluminum, gallium, indium, phosphorus, arsenic, antimony, vanadium and tellurium;

F is at least one element selected from the group consisting of lanthanum, europium, gadolinium, terbium, dysprosium, holmium, erbium, thulium, ytterbium, lutetium, scandium, yttrium, titanium, zirconium, hafnium, niobium, tantalum, aluminum, gallium, indium, thallium, silicon, germanium and less than about 10 ppm lead;

G is at least one element selected from the group consisting of silver, gold, ruthenium, rhodium, palladium, osmium, iridium, platinum and mercury;

Q is at least one of samarium, praseodymium and neodymium, and wherein a is 0.05 to 7, b is 0.1 to 7, c is 0.01 to 5, d is 0 to 12, e is 0 to 5, f is 0 to 5, g is 0 to 0.2, h is 0.01 to 5, i is 0.1 to 12, j is 0 to 12, k is 0 to 12, l is 0 to 12, m is 10 to 15, q is 0 to 2.476 x is the number of oxygen atoms required to satisfy the valence requirements of the other component elements present; and wherein $0.4 < b/(a+h)$, $0.2 < i/(i+j+k+l)$, and, wherein $z = d+i+j+k+l$ and $0.3 \leq (a+h)/z$.

The catalyst of the present invention may be used either supported or unsupported (i.e. the catalyst may comprise a support). Suitable supports are silica, alumina, zirconium, titania, or mixtures thereof. A support typically serves as a binder for the catalyst and results in a stronger (i.e. more attrition resistant) catalyst. However, for commercial applications, an appropriate blend of both the active phase (i.e. the complex of catalytic oxides described above) and the support is crucial to obtain an acceptable activity and hardness (attrition resistance) for the catalyst. Typically, the support comprises between 40 and 60 weight percent of the supported catalyst. In one embodiment of this invention, the support may comprise as little as about 30 weight percent of the supported catalyst. In another embodiment of this invention, the support may comprise as much as about 70 weight percent of the supported catalyst.

In one embodiment the catalyst is supported using a silica sol. Typically, silica sols contain some sodium. In one embodiment, the silica sol contains less than 600 ppm sodium. In another embodiment, the silica sol contains less than 200 ppm sodium. Typically, the average colloidal particle diameter of the silica sol is between about 15 nm and about 50 nm. In one embodiment of this invention, the average colloidal particle diameter of the silica sol is about 10 nm and can be as low as about 4 nm. In another embodiment of this invention, the average colloidal particle diameter of the silica sol is about 100 nm. In another embodiment of this invention, the average colloidal particle diameter of the silica sol is about 20 nm. In another embodiment of this invention, the average colloidal particle diameter of the silica sol is about 40 nm.

Nitrogen Utilization

The instant invention also relates a process and novel catalyst for the production of acrylonitrile, acetonitrile and hydrogen cyanide characterized by the relative yields of acrylonitrile, acetonitrile and hydrogen cyanide produced in the process and/or by the catalyst being defined by the following:

$$\alpha = [(\% \text{ AN} + (3 \times \% \text{ HCN}) + (1.5 \times \% \text{ ACN})) \div \% \text{ PC}] \times 100$$

wherein % AN is the Acrylonitrile Yield and % AN≥82,

% HCN is the Hydrogen Cyanide Yield and % HCN≥5,

% ACN is the Acetonitrile Yield,

% PC is the Propylene Conversion, and

α is greater than 102.5.

In other embodiments, independently % AN is greater than or equal to 82.5; % PC is greater than 90; % PC is greater than 95; % PC is greater than 98; and α is greater than 103. As used herein, "Acrylonitrile Yield" means the percent molar yield of acrylonitrile (expressed as a number without any percent sign) calculated as follows: (moles of acrylonitrile produced÷the moles of propylene fed to the reactor)×100. "Hydrogen Cyanide Yield" means the percent molar yield of hydrogen cyanide (expressed as a number without any percent sign) calculated as follows: [(moles of hydrogen cyanide produced÷3)÷the moles of propylene fed to the reactor]×100. "Acetonitrile Yield" means the percent molar yield of acetonitrile (expressed as a number without any percent sign) calculated as follows: [(moles of acetonitrile produced÷1.5)÷the moles of propylene fed to the reactor]×100. Propylene Conversion means the percent molar conversion of propylene to products and byproducts (expressed as a number without any percent sign) calculated as follows: [(the moles of propylene fed to the reactor minus the moles of propylene exiting the reactor)÷the moles of propylene fed to the reactor]×100.

The "α" is a measure of "nitrogen insertion" or "nitrogen utilization" (i.e. nitrogen from the ammonia combining with propylene to form compounds having the function group "—CN" during the ammoxidation reaction; as such, the greater the "α", the greater overall conversion of the propylene to acrylonitrile, hydrogen cyanide and acetonitrile). The catalyst of the instant invention are characterized by a high "α" (i.e. greater than 102.5) which is a measure of how efficient the catalyst is in utilizing ammonia for the ammoxidation of propylene to acrylonitrile.

Catalyst Preparation:

The catalyst may be prepared by any of the numerous methods of catalyst preparation which are known to those of skill in the art. A typical preparation method will begin with the formation of a mixture of water, a molybdenum source compound and a support material (e.g. silica sol). Separately, source compounds of the remaining elements in the catalyst are combined in water to form a second mixture. These two mixtures are then combined with stirring at a slightly elevated temperature (approximately 65° C.) to form a catalyst precursor slurry. The catalyst precursor slurry is then dried and denitrified and then calcined as described below.

In one embodiment, the elements in the above identified catalyst composition are combined together in an aqueous catalyst precursor slurry, the aqueous precursor slurry so obtained is dried to form a catalyst precursor, and the catalyst precursor is calcined to form the catalyst. However, unique to the process of the instant invention is the following:

(i) combining, in an aqueous solution, source compounds of Bi and Ce, and optionally one or more of Li, Na, K, Rb, Cs, Ca, lanthanum, praseodymium, neodymium, samarium, europium, gadolinium, terbium, dysprosium, holmium, erbium, thulium, ytterbium, lutetium, scandium, yttrium, Pb, and W, to form a mixture (i.e. a first mixture), (ii) adding a source compound of molybdenum to the mixture (i.e. the first mixture) to react with the mixture and form a precipitate slurry, and (iii) combining the precipitate slurry with source compounds of the remaining elements and of the remaining molybdenum in the catalyst to form the aqueous catalyst precursor slurry.

As used herein, "source compounds" are compounds which contain and/or provide one or more of the metals for the mixed metal oxide catalyst composition. As used herein, "remaining elements" or "remaining elements in the catalyst" refers to those elements and the quantity of those elements represented by "A", "D", "E", "F" and "G" in the above formula which were not included in the first mixture. In one embodiment, some elements may be a part of both the first and second mixture. Further, as used herein, "remaining molybdenum" or "remaining molybdenum in the catalyst" refers to that quantity of molybdenum required in the finished catalyst which was not present (i.e. not included in the preparation of) in the precipitate slurry. Lastly, the sum of the quantities of molybdenum provided in the source compounds of molybdenum added in (ii) and (iii) is equal to the total quantity of molybdenum present in the catalyst.

In the above catalyst preparation, the source compounds of the remaining elements and of the remaining molybdenum which are combined with the precipitate slurry may be combined in any order or combination of such remaining elements and remaining molybdenum. In one embodiment, a mixture of the source compounds of the remaining elements and of the remaining molybdenum is combined with the precipitate slurry to form the aqueous catalyst precursor slurry. In another embodiment, (i) a mixture of the source compounds of the remaining elements is combined with the precipitate slurry, and (ii) source compounds of the remaining molybdenum are separately added to the precipitate slurry to form the aqueous catalyst precursor slurry. In another embodiment, source compounds of the remaining elements and of the remaining molybdenum are added individually (i.e. one at a time) to the precipitate slurry. In another embodiment, multiple (i.e. more than one) mixtures of source compounds of the remaining elements and of the remaining molybdenum, wherein each mixture contains one or more of the source compounds of the remaining elements or of the remaining molybdenum, are separately added (i.e. one mixture at a time or multiple mixtures added simultaneously) to the precipitate slurry to form the aqueous catalyst precursor slurry. In yet another embodiment, a mixture of source compounds of the remaining elements is combined with a source compound of molybdenum and the resulting mixture is then added to the precipitate slurry to form the catalyst precursor slurry. In yet another embodiment, the support is silica ($SiO_2$) and the silica is combined with a source compound for the remaining molybdenum prior to combining the remaining molybdenum with the precipitate slurry (i.e. the silica and a source compound for the remaining molybdenum are combined to form a mixture and then this mixture is added to the precipitate slurry, individually or in combination with one or more source compounds of the remaining elements).

In the above catalyst preparation, molybdenum is added both in the preparation of the precipitate slurry and in the preparation of the aqueous catalyst precursor slurry. On an atomic level, the minimum amount of molybdenum added to form the precipitate slurry is determined by the following relationship $$Mo=1.5(Bi+Ce)+0.5(Rb+Li+Na+K+Cs)+(Ca)+1.5 \text{ (sum of the number of atoms of lanthanum, praseodymium, neodymium, samarium, europium, gadolinium, terbium, dysprosium, holmium, erbium, thulium, ytterbium, lutetium, scandium and yttrium)}+(Pb)-(W)$$

Wherein in the above relationship "Mo" is the number of atoms of molybdenum to be added to the first mixture, and "Bi", "Ce", "Rb", "Li', "Na", "K", "Cs", "Ca", "Pb" and "W" are the number of atoms of bismuth, cerium, rubidium, lithium, sodium, potassium, cesium, calcium, lead and tungsten respectively, present in the first mixture.

In the above catalyst preparation, typically, the amount of molybdenum added to the first mixture to form the precipitate slurry is about 20 to 35% of the total molybdenum in the final catalyst. In one embodiment, a source compound for the remaining molybdenum present in the catalyst is added to the mixture of the source compounds of the remaining elements (i.e. the second mixture) prior to the combination of the mixture of the remaining elements with the precipitate slurry to form the catalyst precursor slurry. In other embodiments, a source compound of molybdenum containing the remaining molybdenum present in the catalyst is added to the precipitate slurry either prior to, after or simultaneously with, the mixture of the source compounds of the remaining elements (i.e. the second mixture) in order to form the catalyst precursor slurry.

In the above preparation, source compounds of Bi and Ce, and optionally one or more of Li, Na, K, Rb, Cs, Ca, a rare earth element, Pb and W, are combined in an aqueous solution to form a mixture. In one embodiment, bismuth nitrate and optionally other metal nitrates (i.e. nitrates of Li, Na, K, Rb, Cs, Ca, a rare earth element and/or Pb) are dissolved in an aqueous solution of ceric ammonium nitrate. If tungsten is added, the source compound is typically ammonium paratungstate, $(NH_4)_{10}H_2(W_2O_7)_6$. As used herein, a "rare earth element" means at least one of lanthanum, cerium, praseodymium, neodymium, promethium, samarium, europium, gadolinium, terbium, dysprosium, holmium, erbium, thulium, ytterbium, scandium and yttrium.

Added to the mixture comprising the bismuth and cerium (and optionally one or more of Li, Na, K, Rb, Cs, Ca, a rare earth element, Pb and/or W) is a source compound of molybdenum. In one embodiment this source compound of molybdenum is ammonium heptamolybdate dissolved in water. Upon the addition of the molybdenum source compound to the mixture comprising the bismuth and cerium, a reaction will occur which will result in a precipitate and the resulting mixture is the precipitate slurry.

The precipitate slurry is then combined with a mixture of source compound of the remaining elements of the catalyst and a source compound of molybdenum, to form the aqueous catalyst precursor slurry. The mixture of source compounds of the remaining elements and a source compound of molybdenum may be prepared by combining source compounds of the remaining elements in an aqueous solution (e.g. source compounds are combined in water) and then adding a source compound of molybdenum. In one embodiment this source compound of molybdenum is ammonium heptamolybdate dissolved in water. When combining the precipitate slurry with the remaining elements/molybdenum mixture, the order of addition is not important, i.e. the precipitate slurry may be added to the remaining elements/molybdenum mixture or the remaining elements/molybdenum mixture may be added to the precipitate slurry. The aqueous catalyst precursor slurry is maintained at an elevated temperature.

The amount of aqueous solvent in each of the above described aqueous mixtures and slurries may vary due to the solubilities of the source compounds combined to form the particular mixed metal oxide. The amount of aqueous solvent should at least be sufficient to yield a slurry or mixture of solids and liquids which is able to be stirred.

In any case, the source compounds are preferably combined and/or reacted by a protocol that comprises mixing the source compounds during the combination and/or reaction step. The particular mixing mechanism is not critical, and can include for example, mixing (e.g., stirring or agitating) the components during the reaction by any effective method. Such methods include, for example, agitating the contents of the vessel, for example by shaking, tumbling or oscillating the component-containing vessel. Such methods also include, for example, stirring by using a stirring member located at least partially within the reaction vessel and a driving force coupled to the stirring member or to the reaction vessel to provide relative motion between the stirring member and the reaction vessel. The stirring member can be a shaft-driven and/or shaft-supported stirring member. The driving force can be directly coupled to the stirring member or can be indirectly coupled to the stirring member (e.g., via magnetic coupling). The mixing is generally preferably sufficient to mix the components to allow for efficient reaction between components of the reaction medium to form a more homogeneous reaction medium (e.g., and resulting in a more homogeneous mixed metal oxide precursor) as compared to an unmixed reaction. This results in more efficient consumption of starting materials and in a more uniform mixed metal oxide product. Mixing the precipitate slurry during the reaction step also causes the precipitate to form in solution rather than on the sides of the reaction vessel. More advantageously, having the precipitate form in solution allows for particle growth on all faces of the particle rather than the limited exposed faces when the growth occurs out from the reaction vessel wall.

A source compound of molybdenum may include molybdenum (VI) oxide ($MoO_3$), ammonium heptamolybdate or molybdic acid. The source compound of molybdenum may be introduced from any molybdenum oxide such as dioxide, trioxide, pentoxide or heptaoxide. However, it is preferred that a hydrolyzable or decomposable molybdenum salt be utilized as source compound of molybdenum.

Typical source compounds for bismuth, cerium and the remaining elements of the catalyst are nitrate salts of the metals. Such nitrate salts are readily available and easily soluble. A source compound of bismuth may include an oxide or a salt which upon calcination will yield the oxide. The water soluble salts which are easily dispersed but form stable oxides upon heat treating are preferred. In one embodiment the source compound of bismuth is bismuth nitrate, $Bi(NO_3)_3 \cdot 5H_2O$ A source compound of cerium may include an oxide or a salt which upon calcination will yield the oxide. The water soluble salts which are easily dispersed but form stable oxides upon heat treating are preferred. In one embodiment the source compound of cerium is ceric ammonium nitrate, $(NH_4)_2Ce(NO_3)_6$. In another embodiment the source compound of cerium is cerium nitrate, $Ce(NO_3)_3 \cdot 6H_2O$.

A source compound of iron may be obtained from any compound of iron which, upon calcination will result in the oxide. As with the other elements, water soluble salts are preferred for the ease with which they may be uniformly dispersed within the catalyst. Most preferred is ferric nitrate.

Source compounds for the remaining elements may be derived from any suitable source. For example, cobalt, nickel and magnesium may be introduced into the catalyst using nitrate salts. Additionally, magnesium may be introduced into the catalyst as an insoluble carbonate or hydroxide which upon heat treating results in an oxide. Phosphorus may be introduced in the catalyst as an alkaline metal salt or alkaline earth metal salt or the ammonium salt but is preferably introduced as phosphoric acid.

Source compounds for the alkali components of the catalyst may be introduced into the catalyst as an oxide or as a salt which upon calcination will yield the oxide.

Solvents, in addition to water, may be used to prepare the mixed metal oxides according to the invention include, but are not limited to, alcohols such as methanol, ethanol, propanol, diols (e.g. ethylene glycol, propylene glycol, etc.), organic acids such as acetic acid, as well as other polar solvents known in the art. The metal source compounds are at least partially soluble in the solvent.

As previously noted, the catalyst of the present invention may be used either supported or unsupported (i.e. the catalyst may comprise a support). Suitable supports are silica, alumina, zirconia, titania, or mixtures thereof. The support may be added any time prior to the catalyst precursor slurry being dried. The support may be added at any time during or after the preparation of any mixture of elements, the precipitate slurry or the catalyst precursor slurry. Further the support need not be added in a single point or step (i.e. the support may be added at multiple points in the preparation. In one embodiment, the support is combined with the other ingredients during the preparation of the aqueous catalyst precursor slurry. In one embodiment, the support is added to the precipitate slurry (i.e. after the precipitate slurry is prepared). In one embodiment, the support is combined with the source compound of molybdenum prior to combining the source compound of molybdenum with source compounds of the remaining elements in the catalyst to form the "second mixture" referred to above.

The catalyst precursor slurry is dried and denitrified (i.e. the removal of nitrates) to yield the catalyst precursor. In one embodiment, the catalyst precursor slurry is dried to form catalyst particles. In one embodiment, the catalyst precursor slurry is spray-dried into microspheroidal catalyst particles. In one embodiment the spray dryer outlet temperature of between 110° C. and 350° C. dryer outlet temperature, preferably between 110° C. and 250° C., most preferably between 110° C. and 180° C. In one embodiment the spray dryer is a co-current flow spray dryer (i.e. the particles are sprayed co-current to the gas flow). In another embodiment the spray dryer is countercurrent flow (i.e. the particles are sprayed countercurrent to the gas flow). In another embodiment the spray dryer is a pressure nozzle type spray dryer. In such spray-drying processes, water-containing solid phase particles are sprayed into contact with hot gas (usually air) so as to vaporize the water. The drying is controlled by the temperature of the gas and the distance the particles travel in contact with the gas. It is generally undesirable to adjust these parameters to achieve too rapid drying as this results in a tendency to form dried skins on the partially dried particles of the solid phase which are subsequently ruptured as water occluded within the particles vaporizes and attempts to escape. By the same token, it is desirable to provide the catalyst in a form having as little occluded water as possible. Therefore, where a fluidized bed reactor is to be used and microspheroidal particles are desired, it is advisable to choose the conditions of spray-drying with a view to achieving complete drying without particle rupture. The dried catalyst material is then heated to remove any remaining nitrates. The denitrification temperature may range from 100° C. to 500° C., preferably 250° C. to 450° C.

Finally, the dried and denitrified catalyst precursor is calcined to form the finished catalyst. In one embodiment, the calcination is effected in air. In another embodiment, the calcination is effected in an inert atmosphere. In one embodiment, the catalyst precursor is calcined in nitrogen. Calcination conditions include temperatures ranging from about 300° C. to about 700° C., more preferably from about 350° C. to about 650° C., and in some embodiments, the calcination may be at about 600° C. In one embodiment, calcination may be completed in multiple stages of increasing temperatures. In one embodiment, a first calcination step is conducted at a temperature in the range of about 300° C. to about 450° C., followed by a second calcination step conducted at a temperature in the range of about 500° C. to about 650° C.

Ammoxidation Process

The catalysts of the instant invention are useful in ammoxidation processes for the conversion of an olefin selected from the group consisting of propylene, isobutylene or mixtures thereof, to acrylonitrile, methacrylonitrile and mixtures thereof, respectively, by reacting in the vapor phase at an elevated temperature and pressure said olefin with a molecular oxygen containing gas and ammonia in the presence of the catalyst. The catalysts of the instant invention are also useful for the ammoxidation of methanol to hydrogen cyanide and the ammoxidation of ethanol to acetonitrile. In one embodiment employing the catalysts described herein, methanol and/or ethanol can be co-fed to a process for the ammoxidation of propylene, isobutylene or mixtures thereof to acrylonitrile, methacrylonitrile or mixtures thereof, in order to increase the production of hydrogen cyanide and/or acetonitrile co-products resulting from such process.

Preferably, the ammoxidation reaction is performed in a fluid bed reactor although other types of reactors such as transport line reactors are envisioned. Fluid bed reactors, for the manufacture of acrylonitrile are well known in the prior art. For example, the reactor design set forth in U.S. Pat. No. 3,230,246, herein incorporated by reference, is suitable.

Conditions for the ammoxidation reaction to occur are also well known in the prior art as evidenced by U.S. Pat. Nos. 5,093,299; 4,863,891; 4,767,878 and 4,503,001; herein incorporated by reference. Typically, the ammoxidation process is performed by contacting propylene or isobutylene in the presence of ammonia and oxygen with a fluid bed catalyst at an elevated temperature to produce the acrylonitrile or methacrylonitrile. Any source of oxygen may be employed. For economic reasons, however, it is preferred to use air. The typical molar ratio of the oxygen to olefin in the feed should range from 0.5:1 to 4:1, preferably from 1:1 to 3:1.

The molar ratio of ammonia to olefin in the feed in the reaction may vary from between 0.5:1 to 2:1. There is really no upper limit for the ammonia-olefin ratio, but there is generally no reason to exceed a ratio of 2:1 for economic reasons. Suitable feed ratios for use with the catalyst of the instant invention for the production of acrylonitrile from propylene are an ammonia to propylene ratio in the range of 0.9:1 to 1.3:1, and air to propylene ratio of 8.0:1 to 12.0:1. The catalyst of the instant invention is able to provide high yields of acrylonitrile at relatively low ammonia to propylene feed ratios of about 1:1 to about 1.05:1. These "low ammonia conditions" help to reduce unreacted ammonia in the reactor effluent, a condition known as "ammonia breakthrough", which subsequently helps to reduce process wastes. Specifically, unreacted ammonia must be removed from the reactor effluent prior to the recovery of the acrylonitrile. Unreacted ammonia is typically removed by contacting the reactor effluent with sulfuric acid to yield ammonium sulfate or by contacting the reactor effluent with acrylic acid to yield ammonium acrylate, which in both cases results in a process waste stream to be treated and/or disposed.

The reaction is carried out at a temperature of between the ranges of about 260° to 600° C., preferred ranges being 310° to 500° C., especially preferred being 350° to 480° C. The contact time, although not critical, is generally in the range of 0.1 to 50 seconds, with preference being to a contact time of 1 to 15 seconds.

The products of reaction may be recovered and purified by any of the methods known to those skilled in the art. One such method involves scrubbing the effluent gases from the reactor with cold water or an appropriate solvent to remove the products of the reaction and then purifying the reaction product by distillation.

The primary utility of the catalyst prepared by the process of the instant invention is for the ammoxidation of propylene to acrylonitrile. Other utilities include any of the ammoxidation of propane to acrylonitrile, the ammoxidation of an alcohol selected from the group consisting of methanol, ethanol or mixtures thereof, to hydrogen cyanide (HCN), acetonitrile, and mixtures thereof, and the ammoxidation of glycerol to acrylonitrile.

The catalyst prepared by the process of the instant invention may also be used for the oxidation of propylene to acrolein and/or acrylic acid. Such processes are typically two stage processes, wherein propylene is converted in the presence of a catalyst to primarily acrolein in the first stage and the acrolein is converted in the presence of a catalyst to primarily acrylic acid in the second stage. The catalyst described herein is suitable for use in the first stage for the oxidation of propylene to acrolein.

Modifying HCN Production During Ammoxidation

In one embodiment of the instant invention, the yield of hydrogen cyanide is increased relative to the amount of acrylonitrile and methacrylonitrile produced in the process by the addition to the catalyst of at least one alkali molybdate compound represented by the formula:

$$A_2Mo_2O_{4+3(z-1)}$$

wherein A is Rb, Li, Na, K, Cs, or a mixture thereof, and z is from 1 to about 8.

The alkali molybdate compound may be unsupported or supported on a suitable carrier such as silica, alumina, zirconia, titania, or mixtures thereof. If supported, the support or carrier comprises between 1 wt % to 99 wt % of the alkali molybdate compound and support combination. The amount of said alkali molybdate compound added to the catalyst is in the range of 0.01 wt % to about 10 wt %, relative to the weight of said catalyst composition.

For the catalyst systems previously described herein (i.e. defined by 0.4<b/(a+h) and 0.3≤(a+h)/d), the addition of the alkali molybdate is especially beneficial to increase the level of nitrogen insertion or nitrogen utilization, previously described above as "α", which is a measure of how efficient a catalyst is in utilizing ammonia for the ammoxidation of propylene to acrylonitrile. The catalysts of the instant invention are characterized by a high "α" (i.e. greater than 102.5) which is a measure of how efficient the catalyst is in utilizing ammonia for the ammoxidation of propylene to acrylonitrile.

Further, where an alkali molybdate compound has been added to the catalyst for the purpose of increasing the hydrogen cyanide production, this trend is reversible by the addition of a molybdenum oxide compound selected from the group consisting of $MoO_3$, ammonium molybdate, ammonium heptamolybdate, ammonium dimolybdate and mixtures thereof to the catalyst and alkali molybdate mixture catalyzing the ammoxidation process. Thus the addition of a molybdenum oxide compound to the catalyst and alkali molybdate mixture increases the yield of acrylonitrile and methacrylonitrile relative to the amount of hydrogen cyanide produced in the process (i.e. the amount of acrylonitrile and/or methacrylonitrile produced will increase to approach or be restored to the to the levels which existed prior to the addition of the alkali molybdate and the amount of hydrogen cyanide will decrease to approach or be restored to the levels which existed prior to the addition of the alkali molybdate). The molybdenum oxide compound may be unsupported or may be supported on a suitable carrier such as silica, alumina, zirconia, titania, or mixtures thereof. If supported, the support or carrier comprises between 1 wt % to 99 wt % of the molybdenum oxide compound and support combination. The amount of said molybdenum oxide compound added to the catalyst is in the range of 0.01 wt % to about 10 wt %, relative to the weight of said catalyst composition.

The alkali molybdate compound and/or molybdenum oxide compound may be added to the catalyst either in situ, i.e. while the catalyst is operating in the reactor, or may be added to the catalyst external to the reactor. In one embodiment, the alkali molybdate compound or molybdenum oxide compound is added to (i.e. mixed with) fresh fluid-bed ammoxidation catalyst which is then added to the reactor as "make-up" catalyst to maintain catalyst bed height in the reactor and replace catalyst which is loss from the reactor in the effluent or due to attrition.

SPECIFIC EMBODIMENTS

In order to illustrate the instant invention, catalyst prepared in accordance with the instant invention were evaluated and compared under similar reaction conditions to similar catalysts prepared by prior art methods outside the scope of the instant invention. These examples are provided for illustrative purposes only. Catalyst compositions, for each example, are as shown after the example number. Examples designated with a "C" are comparative examples.

Example
C1—Ni4Mg3Fe0.9Rb0.2Cr0.05Bi1.25Ce1.25Mo12.85Ox+50 wt % 38.2 nm SiO2

Reaction mixture A was prepared by heating 1370.303 ml of deionized water to 65° C. and then adding with stirring over 30 minutes ammonium heptamolybdate (1245.730 g) to form a clear colorless solution.

Reaction mixture B was prepared by heating 257.123 ml of deionized water to 55° C. and then adding with stirring Fe(NO3)3.9H2O (285.052 g), Ni(NO3)2.6H20 (911.870 g), Mg(NO3)2.6H2O (603.024 g), and Cr(NO3)3.9H2O (15.685 g).

Reaction mixture C was prepared by heating 586.185 ml of deionized water to 65° C. and then adding with stirring over 30 minutes ammonium heptamolybdate (532.896 g) to form a clear colorless solution.

Reaction mixture D was prepared by (i) heating 1074.497 g of 50 wt % aqueous (NH4)2Ce(NO3)6 solution to 55° C., (ii) while the solution was stirring and heating, sequentially adding Bi(NO3)3.5H2O (475.357 g) and RbNO3 (23.121 g).

Reaction mixture E was prepared by adding with stirring, silica sol (5487.8 g, 41 wt % silica) to Reaction mixture A, followed by the addition of Reaction mixture B.

Reaction mixture F was prepared by adding reaction mixture C to reaction mixture D, which resulted in precipitation of an orange solid (this resulting mixture was the precipitate slurry). The stirring of the precipitate slurry was continued for 15 minutes while the temperature was maintained in the 50-55° C. range.

Reaction mixture F was then added to reaction mixture E to form the final catalyst precursor slurry.

The catalyst precursor slurry was allowed to stir for one hour while it cooled to approximately 40° C. It was then homogenized in a blender for 3 minutes at 5000 rpm. The slurry was then spray dried in a spray dryer at an inlet/outlet temperature of 325/140° C. The resulting powder was denitrified by heat treating for 3 hours in air at 290° C., followed by an additional 3 hours at 425° C. The powder was then calcined in air for 3 hours at 560° C.

Example
C2—Ni$_6$Mg$_1$Fe$_{0.7}$Rb$_{0.1}$Cr$_{0.05}$Bi$_{0.83}$Ce$_{1.67}$Mo$_{12.85}$O$_x$+50 wt % 38.2 nm SiO$_2$ Reaction mixture A was prepared by heating 304.303 ml of deionized water to 65° C. and then adding with stirring over 30 minutes ammonium heptamolybdate (276.639 g) to form a clear colorless solution.

Reaction mixture B was prepared by heating 38.310 ml of deionized water to 55° C. and then adding with stirring Fe(NO$_3$)$_3$.9H$_2$O (48.962 g), Ni(NO$_3$)$_2$.6H$_2$O (302.070 g), Mg(NO$_3$)$_2$.6H$_2$O (44.391 g), and Cr(NO$_3$)$_3$.9H$_2$O (11.547 g).

Reaction mixture C was prepared by heating 127.774 ml of deionized water to 65° C. and then adding with stirring over 30 minutes ammonium heptamolybdate (116.158 g) to form a clear colorless solution.

Reaction mixture D was prepared by (i) heating 317.026 g of 50 wt % aqueous (NH$_4$)$_2$Ce(NO$_3$)$_6$ solution to 55° C., (ii) while the solution was stirring and heating, sequentially adding Bi(NO$_3$)$_3$.5H$_2$O (69.706 g) and RbNO$_3$ (8.510 g).

Reaction mixture E was prepared by adding with stirring, silica sol (1219.5 g, 41 wt % silica) to Reaction mixture A, followed by the addition of Reaction mixture B.

Reaction mixture F was prepared by adding reaction mixture C to reaction mixture D, which resulted in precipitation of an orange solid (this resulting mixture was the precipitate slurry). The stirring of the precipitate slurry was continued for 15 minutes while the temperature was maintained in the 50-55° C. range.

Reaction mixture F was then added to reaction mixture E to form the final catalyst precursor slurry.

The catalyst precursor slurry was allowed to stir for one hour while it cooled to approximately 40° C. It was then homogenized in a blender for 3 minutes at 5000 rpm. The slurry was then spray dried in a spray dryer at an inlet/outlet temperature of 325/140° C. The resulting powder was denitrified by heat treating for 3 hours in air at 290° C., followed by an additional 3 hours at 425° C. The powder was then calcined in air for 3 hours at 560° C.

Example 1 and
2—Ni$_4$Mg$_3$Fe$_{1.2}$Rb$_{0.2}$Cr$_{0.05}$Bi$_{1.25}$Ce$_{1.25}$Mo$_{12.85}$O$_x$+
50 wt % 38.2 nm SiO$_2$ Reaction mixture A was prepared by heating 1358.961 ml of deionized water to 65° C. and then adding with stirring over 30 minutes ammonium heptamolybdate (1235.419 g) to form a clear colorless solution.

Reaction mixture B was prepared by heating 265.465 ml of deionized water to 55° C. and then adding with stirring Fe(NO$_3$)$_3$.9H$_2$O (376.923 g), Ni(NO$_3$)$_2$.6H$_2$O (904.322 g), Mg(NO$_3$)$_2$.6H$_2$O (598.033 g), and Cr(NO$_3$)$_3$.9H$_2$O (15.555 g).

Reaction mixture C was prepared by heating 581.333 ml of deionized water to 65° C. and then adding with stirring over 30 minutes ammonium heptamolybdate (528.485 g) to form a clear colorless solution.

Reaction mixture D was prepared by (i) heating 1065.603 g of 50 wt % aqueous (NH$_4$)$_2$Ce(NO$_3$)$_6$ solution to 55° C., (ii) while the solution was stirring and heating, sequentially adding Bi(NO$_3$)$_3$.5H$_2$O (471.422 g) and RbNO$_3$ (22.930 g).

Reaction mixture E was prepared by adding with stirring, silica sol (5487.8 g, 41 wt % silica) to Reaction mixture A, followed by the addition of Reaction mixture B.

Reaction mixture F was prepared by adding reaction mixture C to reaction mixture D, which resulted in precipitation of an orange solid (this resulting mixture was the precipitate slurry). The stirring of the precipitate slurry was continued for 15 minutes while the temperature was maintained in the 50-55° C. range.

Reaction mixture F was then added to reaction mixture E to form the final catalyst precursor slurry.

The catalyst precursor slurry was allowed to stir for one hour while it cooled to approximately 40° C. It was then homogenized in a blender for 3 minutes at 5000 rpm. The slurry was then spray dried in a spray dryer at an inlet/outlet temperature of 325/140° C. The resulting powder was denitrified by heat treating for 3 hours in air at 290° C., followed by an additional 3 hours at 425° C. The powder was then calcined in air for 3 hours at 560° C.

Example 3 and
4—Ni$_6$Mg$_1$Fe$_1$Rb$_{0.2}$Cr$_{0.05}$Bi$_1$Ce$_{1.22}$Mo$_{12.505}$O$_x$+50
wt % 38.2 nm SiO$_2$ Reaction mixture A was prepared by heating 1399.413 ml of deionized water to 65° C. and then adding with stirring over 30 minutes ammonium heptamolybdate (1272.194 g) to form a clear colorless solution.

Reaction mixture B was prepared by heating 259.349 ml of deionized water to 55° C. and then adding with stirring Fe(NO$_3$)$_3$.9H$_2$O (320.780 g), Ni(NO$_3$)$_2$.6H$_2$0 (1385.318 g), Mg(NO$_3$)$_2$.6H$_2$O (203.582 g), and Cr(NO$_3$)$_3$.9H$_2$O (15.886 g).

Reaction mixture C was prepared by heating 528.924 ml of deionized water to 65° C. and then adding with stirring over 30 minutes ammonium heptamolybdate (480.840 g) to form a clear colorless solution.

Reaction mixture D was prepared by (i) heating 1062.136 g of 50 wt % aqueous (NH$_4$)$_2$Ce(NO$_3$)$_6$ solution to 55° C., (ii) while the solution was stirring and heating, sequentially adding Bi(NO$_3$)$_3$.5H$_2$O (385.155 g) and RbNO$_3$ (23.417 g).

Reaction mixture E was prepared by adding with stirring, silica sol (5263.2 g, 41 wt % silica) to Reaction mixture A, followed by the addition of Reaction mixture B.

Reaction mixture F was prepared by adding reaction mixture C to reaction mixture D, which resulted in precipitation of an orange solid (this resulting mixture was the precipitate slurry). The stirring of the precipitate slurry was continued for 15 minutes while the temperature was maintained in the 50-55° C. range.

Reaction mixture F was then added to reaction mixture E to form the final catalyst precursor slurry.

The catalyst precursor slurry was allowed to stir for one hour while it cooled to approximately 40° C. It was then homogenized in a blender for 3 minutes at 5000 rpm. The slurry was then spray dried in a spray dryer at an inlet/outlet temperature of 325/140° C. The resulting powder was denitrified by heat treating for 3 hours in air at 290° C., followed by an additional 3 hours at 425° C. The powder was then calcined in air for 3 hours at 560° C.

Example
5—Ni$_4$Mg$_3$Fe$_{1.2}$Rb$_{0.2}$Cr$_{0.05}$Bi$_{1.25}$Ce$_{1.25}$Mo$_{12.730}$O$_x$+
50 wt 38.2 nm SiO$_2$ Reaction mixture A was prepared by heating 150.66 ml of deionized water to 65° C. and then adding with stirring over 30 minutes ammonium heptamolybdate (136.60 g) to form a clear colorless solution.

Reaction mixture B was prepared by heating 29.93 ml of deionized water to 55° C. and then adding with stirring Fe(NO$_3$)$_3$.9H$_2$O (42.2625 g), Ni(NO$_3$)$_2$.6H$_2$O (101.42 g), Mg(NO$_3$)$_2$.6H$_2$O (67.0604 g), and Cr(NO$_3$)$_3$.9H$_2$O (1.7441 g).

Reaction mixture C was prepared by heating 71.75 ml of deionized water to 65° C. and then adding with stirring over 30 minutes ammonium heptamolybdate (59.3332 g) to form a clear colorless solution.

Reaction mixture D was prepared by (i) heating 119.53 g of 50 wt % aqueous (NH$_4$)$_2$Ce(NO$_3$)$_6$ solution to 55° C., (ii) while the solution was stirring and heating, sequentially adding Bi(NO$_3$)$_3$.5H$_2$O (52.8606 g) and RbNO$_3$ (2.7027 g).

Reaction mixture E was prepared by adding with stirring, silica sol (609.76 g, 41 wt % silica) to Reaction mixture A, followed by the addition of Reaction mixture B.

Reaction mixture F was prepared by adding reaction mixture C to reaction mixture D, which resulted in precipitation of an orange solid (this resulting mixture was the precipitate slurry). The stirring of the precipitate slurry was continued for 15 minutes while the temperature was maintained in the 50-55° C. range.

Reaction mixture F was then added to reaction mixture E to form the final catalyst precursor slurry.

The catalyst precursor slurry was allowed to stir for one hour while it cooled to approximately 40° C. It was then homogenized in a blender for 3 minutes at 5000 rpm. The slurry was then spray dried in a spray dryer at an inlet/outlet temperature of 325/140° C. The resulting powder was denitrified by heat treating for 3 hours in air at 290° C., followed by an additional 3 hours at 425° C. The powder was then calcined in air for 3 hours at 560° C.

Example 6—Ni$_4$Mg$_3$Fe$_{1.2}$Rb$_{0.2}$Cr$_{0.05}$Bi$_{1.25}$Ce$_{1.25}$Mo$_{12.130}$O$_x$+ 50 wt % 38.2 nm SiO$_2$ Reaction mixture A was prepared by heating 144.67 ml of deionized water to 65° C. and then adding with stirring over 30 minutes ammonium heptamolybdate (131.32 g) to form a clear colorless solution.

Reaction mixture B was prepared by heating 30.87 ml of deionized water to 55° C. and then adding with stirring Fe(NO$_3$)$_3$.9H$_2$O (43.5883 g), Ni(NO$_3$)$_2$.6H$_2$O (104.57 g), Mg(NO$_3$)$_2$.6H$_2$O (69.1397 g), and Cr(NO$_3$)$_3$.9H$_2$O (1.7983 g).

Reaction mixture C was prepared by heating 74.12 ml of deionized water to 65° C. and then adding with stirring over 30 minutes ammonium heptamolybdate (61.1793 g) to form a clear colorless solution.

Reaction mixture D was prepared by (i) heating 123.30 g of 50 wt % aqueous (NH$_4$)$_2$Ce(NO$_3$)$_6$ solution to 55° C., (ii) while the solution was stirring and heating, sequentially adding Bi(NO$_3$)$_3$.5H$_2$O (54.5021 g) and RbNO$_3$ (2.7847 g).

Reaction mixture E was prepared by adding with stirring, silica sol (609.80 g, 41 wt % silica) to Reaction mixture A, followed by the addition of Reaction mixture B.

Reaction mixture F was prepared by adding reaction mixture C to reaction mixture D, which resulted in precipitation of an orange solid (this resulting mixture was the precipitate slurry). The stirring of the precipitate slurry was continued for 15 minutes while the temperature was maintained in the 50-55° C. range.

Reaction mixture F was then added to reaction mixture E to form the final catalyst precursor slurry.

The catalyst precursor slurry was allowed to stir for one hour while it cooled to approximately 40° C. It was then homogenized in a blender for 3 minutes at 5000 rpm. The slurry was then spray dried in a spray dryer at an inlet/outlet temperature of 325/140° C. The resulting powder was denitrified by heat treating for 3 hours in air at 290° C., followed by an additional 3 hours at 425° C. The powder was then calcined in air for 3 hours at 560° C.

Example 7—Ni4Mg3Fe1.2Rb0.192Cr0.05Bi1.0Sm0.1Ce1.5 Mo12.996Ox+50 wt % 38.2 nm SiO2

Reaction mixture A was prepared by heating 152.49 ml of deionized water to 65° C. and then adding with stirring over 30 minutes ammonium heptamolybdate (139.06 g) to form a clear colorless solution.

Reaction mixture B was prepared by heating 28.35 ml of deionized water to 55° C. and then adding with stirring Fe(NO$_3$)$_3$.9H$_2$O (41.73229 g), Ni(NO$_3$)$_2$.6H$_2$O (100.16 g), Mg(NO$_3$)$_2$.6H$_2$O (66.2090 g), and Cr(NO$_3$)$_3$.9H$_2$O (1.7272 g).

Reaction mixture C was prepared by heating 70.69 ml of deionized water to 65° C. and then adding with stirring over 30 minutes ammonium heptamolybdate (58.4395 g) to form a clear colorless solution.

Reaction mixture D was prepared by (i) heating 141.57 g of 50 wt % aqueous (NH$_4$)$_2$Ce(NO$_3$)$_6$ solution to 55° C., (ii) while the solution was stirring and heating, sequentially adding Bi(NO$_3$)$_3$.5H$_2$O (41.7512 g), RbNO$_3$ (2.4389 g), and Sm(NO$_3$)$_3$.6H$_2$O (3.8270 g).

Reaction mixture E was prepared by adding with stirring, silica sol (609.76 g, 41 wt % silica) to Reaction mixture A, followed by the addition of Reaction mixture B.

Reaction mixture F was prepared by adding reaction mixture C to reaction mixture D, which resulted in precipitation of an orange solid (this resulting mixture was the precipitate slurry). The stirring of the precipitate slurry was continued for 15 minutes while the temperature was maintained in the 50-55° C. range.

Reaction mixture F was then added to reaction mixture E to form the final catalyst precursor slurry.

The catalyst precursor slurry was allowed to stir for one hour while it cooled to approximately 40° C. It was then homogenized in a blender for 3 minutes at 5000 rpm. The slurry was then spray dried in a spray dryer at an inlet/outlet temperature of 325/140° C. The resulting powder was denitrified by heat treating for 3 hours in air at 290° C., followed by an additional 3 hours at 425° C. The powder was then calcined in air for 3 hours at 560° C.

Example 8

The catalyst of Example was prepared using the same preparation as Example 7, except 0.094 grams of K$_2$MoO$_4$ solid crystals was added to the finished catalyst.

Example 9

This Example was a continuation of the catalyst testing of Example 8. After 382 hours on stream, 0.144 grams of MoO3 was added to the Example 8 catalyst and testing for the ammoxidation of propylene to acrylonitrile continued.

Catalyst Testing

All catalyst were tested in a bench scale reactor for the ammoxidation of propylene to acrylonitrile using 30 g of catalyst. All testing was conducted in a 40 cc fluid bed reactor. Propylene was feed into the reactor at the rates shown in Table land Table 3, between 0.080 and 0.100 WWH (i.e. weight of propylene/weight of catalyst/hour). Pressure inside the reactor was maintained at 10 psig. Reaction temperature was 430° C. Samples of reaction products were collected after several days of testing (between about 140 to about 190 hours on stream). Reactor effluent was collected in bubble-type scrubbers containing cold HCl solution. Off-gas rate was measured with soap film meter, and the off-gas composition was determined at the end of the run with the aid of gas chromatograph fitted with a split column gas analyzer. At the end of the recovery run, the entire scrubber liquid was diluted to approximately 200 grams with distilled water. A weighted amount of 2-butanone was used as internal standard in a ~50 gram aliquot of the dilute solution. A 2 μl sample was analyzed in a GC fitted with a flame ionization detector and a Carbowax™ column. The amount of NH$_3$ was determined by titrating the free HCl excess with NaOH solution. Propylene conversions and acrylonitrile yields for the tested catalysts are as shown in Tables 1 and 3. HCN was analyzed by titration with AgNO3 solution after adding caustic iodide.

TABLE 1

Examples of the Invention

| Ex. No. | Catalyst Composition | WWH T° C. HOS | % C= Conv. | % AN Yield | % HCN Yield | % ACN Yield | α |
|---|---|---|---|---|---|---|---|
| C1 | $Ni_4Mg_3Fe_{0.9}Rb_{0.2}Cr_{0.05}Bi_{1.25}Ce_{1.25}Mo_{12.85}O_x$ + 50 wt % 38.2 nm $SiO_2$ | 0.080 430.0 120.6 | 98.1 | 84.6 | 3.6 | 2.1 | 100.5 |
| C2 | $Ni_6Mg_1Fe_{0.7}Rb_{0.1}Cr_{0.05}Bi_{0.83}Ce_{1.67}Mo_{12.85}O_x$ + 50 wt % 38.2 nm $SiO_2$ | 0.100 430.0 347.1 | 99.2 | 82.2 | 5.0 | 2.0 | 101.0 |
| 1 | $Ni_4Mg_3Fe_{1.2}Rb_{0.2}Cr_{0.05}Bi_{1.25}Ce_{1.25}Mo_{12.85}O_x$ + 50 wt % 38.2 nm $SiO_2$ | 0.090 430.0 144.8 | 99.5 | 84.3 | 5.1 | 2.0 | 103.1 |
| 2 | $Ni_4Mg_3Fe_{1.2}Rb_{0.2}Cr_{0.05}Bi_{1.25}Ce_{1.25}Mo_{12.85}O_x$ + 50 wt % 38.2 nm $SiO_2$ | 0.090 430.0 504.0 | 99.1 | 83.4 | 6.3 | 1.7 | 105.8 |
| 3 | $Ni_6Mg_1Fe_1Rb_{0.2}Cr_{0.05}Bi_1Ce_{1.22}Mo_{12.505}O_x$ + 50 wt % 38.2 nm $SiO_2$ | 0.090 430.0 319.4 | 99.2 | 83.7 | 5.0 | 2.1 | 102.7 |
| 4 | $Ni_6Mg_1Fe_1Rb_{0.2}Cr_{0.05}Bi_1Ce_{1.22}Mo_{12.505}O_x$ + 50 wt % 38.2 nm $SiO_2$ | 0.085 440.0 990.0 | 98.5 | 82.9 | 5.8 | 2.0 | 104.9 |
| 5 | $Ni_4Mg_3Fe_{1.2}Rb_{0.2}Cr_{0.05}Bi_{1.25}Ce_{1.25}Mo_{12.730}O_x$ + 50 wt % 38.2 nm $SiO_2$ | 0.090 435.0 190.3 | 98.3 | 82.6 | 6.4 | 1.6 | 105.8 |
| 6 | $Ni_4Mg_3Fe_{1.2}Rb_{0.2}Cr_{0.05}Bi_{1.25}Ce_{1.25}Mo_{12.130}O_x$ + 50 wt % 38.2 nm $SiO_2$ | 0.090 430.0 290.5 | 98.2 | 82.3 | 6.1 | 2.1 | 105.7 |
| 7 | $Ni_4Mg_3Fe_{1.2}Rb_{0.192}Cr_{0.05}Bi_{1.0}Sm_{0.1}Ce_{1.5}Mo_{12.996}O_x$ + 50 wt % 38.2 nm $SiO_2$ | 0.100 435.0 237 | 98.9 | 82.8 | 5.7 | 1.9 | 103.9 |

TABLE 2

| Ex. No. | Catalyst Composition | b/(a + h) | (a + h)/d | m-[(3a + 2b + c + 2d + 3h + 3n)/2] |
|---|---|---|---|---|
| C1 | $Ni_4Mg_3Fe_{0.9}Rb_{0.2}Cr_{0.05}Bi_{1.25}Ce_{1.25}Mo_{12.85}O_x$ + 50 wt % 38.2 nm $SiO_2$ | 0.36 | 0.357 | 1.025 |
| C2 | $Ni_6Mg_1Fe_{0.7}Rb_{0.1}Cr_{0.05}Bi_{0.83}Ce_{1.67}Mo_{12.85}O_x$ + 50 wt % 38.2 nm $SiO_2$ | 0.28 | 0.357 | 1.275 |
| 1 | $Ni_4Mg_3Fe_{1.2}Rb_{0.2}Cr_{0.05}Bi_{1.25}Ce_{1.25}Mo_{12.85}O_x$ + 50 wt % 38.2 nm $SiO_2$ | 0.48 | 0.357 | 0.725 |
| 2 | $Ni_4Mg_3Fe_{1.2}Rb_{0.2}Cr_{0.05}Bi_{1.25}Ce_{1.25}Mo_{12.85}O_x$ + 50 wt % 38.2 nm $SiO_2$ | 0.48 | 0.357 | 0.725 |
| 3 | $Ni_6Mg_1Fe_1Rb_{0.2}Cr_{0.05}Bi_1Ce_{1.22}Mo_{12.505}O_x$ + 50 wt % 38.2 nm $SiO_2$ | 0.45 | 0.317 | 1.0 |
| 4 | $Ni6Mg_1Fe_1Rb_{0.2}Cr_{0.05}Bi_1Ce_{1.22}Mo_{12.505}O_x$ + 50 wt % 38.2 nm $SiO_2$ | 0.45 | 0.317 | 1.0 |
| 5 | $Ni_4Mg_3Fe_{1.2}Rb_{0.2}Cr_{0.05}Bi_{1.25}Ce_{1.25}Mo_{12.730}O_x$ + 50 wt 38.2 nm $SiO_2$ | 0.48 | 0.357 | 0.6 |
| 6 | $Ni_4Mg_3Fe_{1.2}Rb_{0.2}Cr_{0.05}Bi_{1.25}Ce_{1.25}Mo_{12.130}O_x$ + 50 wt % 38.2 nm $SiO_2$ | 0.48 | 0.357 | 0 |
| 7 | $Ni_4Mg_3Fe_{1.2}Rb_{0.192}Cr_{0.05}Bi_{1.0}Sm_{0.1}Ce_{1.5}Mo_{12.996}O_x$ + 50 wt % 38.2 nm $SiO_2$ | 0.48 | 0.357 | 0.875 |

TABLE 3

Alkali Molybdate & Molybdenum Oxide Compound Addition

| Ex. No. | Catalyst Composition | WWH T° C. HOS | % C= Conv. | % AN Yield | % HCN Yield | % ACN Yield | α |
|---|---|---|---|---|---|---|---|
| 7 | $Ni_4Mg_3Fe_{1.2}Rb_{0.192}Cr_{0.05}Bi_{1.0}Sm_{0.1}Ce_{1.5}Mo_{12.996}O_x$ + 50 wt % 38.2 nm $SiO_2$ | 0.100 435.0 237 | 98.9 | 82.8 | 5.7 | 1.9 | 103.9 |

TABLE 3-continued

Alkali Molybdate & Molybdenum Oxide Compound Addition

| Ex. No. | Catalyst Composition | WWH T° C. HOS | % C= Conv. | % AN Yield | % HCN Yield | % ACN Yield | α |
|---|---|---|---|---|---|---|---|
| 8 | $Ni_4Mg_3Fe_{1.2}Rb_{0.192}Cr_{0.05}Bi_{1.0}Sm_{0.1}Ce_{1.5}Mo_{12.996}O_x$ + 50 wt % 38.2 nm $SiO_2$ + 0.094 g $K_2MoO_4$ | 0.100 432.0 216 | 99.4 | 82.6 | 6.6 | 1.9 | 105.8 |
| 9 | Example 8 + 0.144 g MoO3 added after 382 hours on stream | 0.100 430.0 2.5 | 99.1 | 84.0 | 5.2 | 2.3 | 103.9 |

Notes for Tables 1, 2 and 3 (where applicable):
1. "WWH" is weight of propylene per weight of catalyst per hour in the feed
2. "T° C." is the reactor temperature in centigrade
3. "HOS" is "hours on stream.
4. "% $C_3^=$Conv" or "% PC" is the Propylene Conversion (i.e. mole percent per pass conversion of propylene to all products).
5. "% AN Yield" is percent acrylonitrile yield.
6. "% AN Yield" is percent acrylonitrile yield.
7. "% Aceto Yield" is the Acetonitrile Yield
8. "α" is calculated as follows: α=[(% AN+(3×% HCN)+(1.5×% ACN))÷% PC]×100
9. "b/(a+h) is the ratio in the composition of atoms of iron to atoms of bismuth plus atoms of cerium.
10. "(a+h)/d" is the ratio in the composition of atoms of bismuth plus atoms of cerium to atoms of the D elements (i.e. nickel, cobalt, manganese, zinc, magnesium, calcium, strontium, cadmium and barium).
11. for catalysts meeting the formula description set forth herein, "m−[(3a+2b+c+2d+3h+3n)/2]" is the numerical value obtained by subtracting from the number of atoms of molybdenum (subscript "m" from the formula) the sum of [(3×the number of atoms of bismuth 0+(2×the number of atoms of iron)+(the number of atoms of lithium, sodium, potassium, rubidium and cesium)+(2×the number of atoms of nickel, cobalt, manganese, zinc, magnesium, calcium, strontium, cadmium, and barium)+(3×the number of atoms of cerium)+(3×the number of atoms of chromium)] divided by 2.

The present invention is directed to an improved and novel mixed metal oxide catalyst for the ammoxidation of propylene and/or isobutylene. This improved catalyst provides greater overall conversion of the propylene and/or isobutylene to hydrogen cyanide while maintaining the acrylonitrile and/or methacrylonitrile production levels at substantially the same level as prior art catalysts.

The data in Tables 1 and 2 clearly shows the benefit of the present invention. Examples 1 through 6 have "b/(a+h)" and "(a+h)/d" values within the scope of the claimed invention (i.e. 0.4<b/(a+h) and 0.3≤(a+h)/d exhibit greater hydrogen cyanide yield (roughly 1 to 3% higher) than those catalysts of C1 through C2 which are outside one or both of the claimed "b/(a+h)" and "(a+h)/d" ranges.

The data in Table 3 clearly demonstrates one embodiment of this invention. Specifically, for the ammoxidation of propylene to acrylonitrile with hydrogen cyanide produced as a co-product when a catalyst of the invention (i.e. the composition of Example 7) is combined with an alkali molybdate (i.e. the mixture of Example 8) there will be a further increase in the yield of HCN and a further increase in nitrogen efficiency as shown by an increase in the α factor. As shown in Example 9 this effect may be reversed.

Example 9 demonstrates that the catalyst mixture of Example 8 can be reverted to a state that provides high yield of acrylonitrile by the addition of molybdenum oxide (i.e. in Example 9 the catalyst reverted to the performance of base composition exemplified as Example 7).

While the foregoing description and the above embodiments are typical for the practice of the instant invention, it is evident that many alternatives, modifications, and variations will be apparent to those skilled in the art in light of this description. Accordingly, it is intended that all such alternatives, modifications and variations are embraced by and fall within the spirit and broad scope of the appended claims.

The claimed invention is:

1. A catalytic composition comprising a complex of metal oxides wherein the relative ratios of the listed elements in said catalyst are represented by the following formula:

$$Mo_mBi_aFe_bA_cD_dE_eF_fG_gCe_hCr_nQ_qO_x$$

wherein A is at least one element selected from the group consisting of lithium, sodium, potassium, rubidium and cesium;
  D is at least one element selected from the group consisting of nickel, cobalt, manganese, zinc, magnesium, calcium, strontium, cadmium and barium;
  E is at least one element selected from the group consisting of tungsten, boron, aluminum, gallium, indium, phosphorus, arsenic, antimony, vanadium and tellurium;
  F is at least one element selected from the group consisting of lanthanum, europium, gadolinium, terbium, dysprosium, holmium, erbium, thulium, ytterbium, lutetium, scandium, yttrium, titanium, zirconium, hafnium, niobium, tantalum, aluminum, gallium, indium, thallium, silicon, lead and germanium;
  G is at least one element selected from the group consisting of silver, gold, ruthenium, rhodium, palladium, osmium, iridium, platinum and mercury;
  Q is at least one of samarium, praseodymium and neodymium; and
  a, b, c, d, e, f, g, h, n, m and x are, respectively, the atomic ratios of bismuth (Bi), iron (Fe), A, D, E, F, G, cerium (Ce), chromium (Cr), molybdenum (Mo) and oxygen (O), relative to "m" atoms of molybdenum (Mo),
  wherein a is 0.05 to 7,
  b is 0.1 to 7,
  c is 0 to 5,
  d is 0.1 to 12,
  e is 0 to 5,
  f is 0 to 5,
  g is 0 to 0.2,
  h is 0.01 to 5,
  m is 10 to 15, n is 0 to 5, q is 0 to 2.476, and x is the number of oxygen atoms required to satisfy the valence requirements of the other component elements present; and wherein $0.4 < b/(a+h)$ and $0.3 \leq (a+h)/d$; and wherein $0 \leq m-(3a+2b+c+2d+3h+3n)/2 \leq 1.0$.

2. The catalyst composition of claim 1, wherein $0.3 \leq (a+h)/d \leq 1$.

3. The catalyst composition of claim 1, wherein $0.45 \leq (a+h)/d \leq 1$.

4. The catalyst composition of claim 1, wherein $0.8 \leq h/b \leq 5$.

5. The catalyst composition of claim 1, wherein $0.5 \leq a/h < 1.5$.

6. The catalyst composition of claim 1, wherein $0 \leq q/(a+h+q)$ and $q/(a+h+q) < 0.16$.

7. The catalyst composition of claim 1 wherein D is nickel.

8. The catalyst composition of claim 1, additionally comprising at least one alkali molybdate compound represented by the formula:

$$A_2Mo_zO_{4+3(z-1)}$$

wherein A is Rb, Li, Na, K, Cs, or a mixture thereof, z is from 1 to about 8.

9. The alkali molybdate compound of claim 8, wherein the alkali molybdate compound comprises a support selected from the group consisting of silica, alumina, zirconia, titania, or mixtures thereof, and wherein the support comprises between 1 wt % to 99 wt % of the molybdate and support combination.

10. The catalyst composition of claim 8, wherein the catalyst composition comprises between of 0.01 wt % to about 10 wt % of the alkali molybdate compound relative to the total weight of said catalyst composition.

11. The catalyst composition of claim 1, wherein the catalytic composition when utilized as a catalyst for the production of acrylonitrile, acetonitrile and hydrogen cyanide in a process comprising contacting at an elevated temperature, propylene, ammonia and oxygen in the vapor phase in the presence of a catalyst, the relative yields of acrylonitrile, acetonitrile and hydrogen cyanide from said process are defined by the following:

$$\alpha = [(\% \text{ AN} + (3 \times \% \text{ HCN}) + (1.5 \times \% \text{ ACN})) \div \% \text{ PC}] \times 100$$

wherein % AN is the Acrylonitrile Yield and % AN $\geq 82$,

% HCN is the Hydrogen Cyanide Yield and % HCN $\geq 5\%$

% ACN is the Acetonitrile Yield,

% PC is the Propylene Conversion, and $\alpha$ is greater than 102.5.

12. A process for the conversion of an olefin selected from the group consisting of propylene, isobutylene and mixtures thereof, to acrylonitrile, methacrylonitrile, and mixtures thereof, with hydrogen cyanide produced as a co-product, by reacting in the vapor phase at an elevated temperature and pressure said olefin with a molecular oxygen containing gas and ammonia in the presence of a catalyst wherein the relative ratios of the listed elements in said catalyst are represented by the following formula:

$$Mo_mBi_aFe_bA_cD_dE_eF_fG_gCe_hCr_nQ_qO_x$$

wherein A is at least one element selected from the group consisting of lithium, sodium, potassium, rubidium and cesium;

D is at least one element selected from the group consisting of nickel, cobalt, manganese, zinc, magnesium, calcium, strontium, cadmium and barium;

E is at least one element selected from the group consisting of tungsten, boron, aluminum, gallium, indium, phosphorus, arsenic, antimony, vanadium and tellurium;

F is at least one element selected from the group consisting of lanthanum, europium, gadolinium, terbium, dysprosium, holmium, erbium thulium, ytterbium, lutetium, scandium, yttrium, titanium, zirconium, hafnium, niobium, tantalum, aluminum, gallium, indium, thallium, silicon, lead and germanium;

G is at least one element selected from the group consisting of silver, gold, ruthenium, rhodium, palladium, osmium, iridium, platinum and mercury;

Q is at least one of samarium, praseodymium and neodymium and a, b, c, d, e, f, g, h, n, m and x are, respectively, the atomic ratios of bismuth (Bi), iron (Fe), A, D, E, F, G, cerium (Ce), chromium (Cr), molybdenum (Mo) and oxygen (O), relative to "m" atoms of molybdenum (Mo), wherein a is 0.05 to 7, b is 0.1 to 7, c is 0 to 5, d is 0.1 to 12, e is 0 to 5, f is 0 to 5, g is 0 to 0.2, h is 0.01 to 5, m is 10 to 15, n is from 0 to 5, q is 0 to 2.476 and x is the number of oxygen atoms required to satisfy the valence requirements of the other component elements present; and wherein $0.4 < b/(a+h)$ and $0.3 \leq (a+h)/d$; and wherein $0 \leq m-(3a+2b+c+2d+3h+3n)/2 \leq 1.0$.

13. The process of claim 12, wherein the yield of hydrogen cyanide is increased relative to the amount of acrylonitrile and methacrylonitrile produced in the process by the addition to the catalyst of at least one alkali molybdate compound represented by the formula:

$$A_2Mo_zO_{4+3(z-1)}$$

wherein A is Rb, Li, Na, K, Cs, or a mixture thereof, and z is from 1 to about 8.

14. The process of claim 13, wherein the catalyst composition comprises between of 0.01 wt % to about 10 wt % of the alkali molybdate compound relative to the total weight of said catalyst composition.

15. The process of claim 12, wherein the yield of acrylonitrile and methacrylonitrile is increased relative to the amount of hydrogen cyanide produced in the process by the addition to the catalyst of a molybdenum oxide compound selected from the group consisting of $MoO_3$, ammonium molybdate, ammonium heptamolybdate, ammonium dimolybdate and mixtures thereof.

16. The process of claim 15, wherein the amount of said molybdenum oxide compound added to the catalyst is in the range of 0.01 wt % to about 10 wt %, relative to the weight of said catalyst.

17. The process of claim 12, wherein $0.3 \leq (a+h)/d \leq 1$ in the catalyst.

18. The process of claim 12, wherein $0.45 \leq (a+h)/d \leq 1$ in the catalyst.

19. The process of claim 12, wherein 0.8≤h/b≤5 in the catalyst.

20. The process of claim 12, wherein 0.5≤a/h<1.5 in the catalyst.

21. The process of claim 12, wherein 0≤q/(a+h+q) and q/(a+h+q)<0.16 in the catalyst.

22. The process of claim 12, wherein D is nickel in the catalyst.

23. The process of claim 12, wherein said process is defined by the following:

$$\alpha = [(\% \text{ AN} + (3 \times \% \text{ HCN}) + (1.5 \times \% \text{ ACN})) \div \% \text{ PC}] \times 100$$

wherein % AN is the Acrylonitrile Yield and % AN≥82,
% HCN is the Hydrogen Cyanide Yield and % HCN≥5%
ACN is the Acetonitrile Yield,
% PC is the Propylene Conversion, and
α is greater than 102.5.

* * * * *